(12) United States Patent
Caputo et al.

(10) Patent No.: US 11,246,869 B2
(45) Date of Patent: Feb. 15, 2022

(54) PROCESS FOR THE PREPARATION OF RALTEGRAVIR

(71) Applicant: CAMBREX PROFARMACO MILANO S.R.L., Paullo (IT)

(72) Inventors: Francesco Caputo, Paullo (IT); Daniele Vigo, Paullo (IT); Oreste Piccolo, Sirtori (IT)

(73) Assignee: CAMBREX PROFARMACO MILANO S.R.L., Paullo (IT)

( * ) Notice: Subject to any disclaimer, the term of this patent is extended or adjusted under 35 U.S.C. 154(b) by 90 days.

(21) Appl. No.: 16/764,026

(22) PCT Filed: Nov. 13, 2018

(86) PCT No.: PCT/EP2018/081042
§ 371 (c)(1),
(2) Date: May 14, 2020

(87) PCT Pub. No.: WO2019/096773
PCT Pub. Date: May 23, 2019

(65) Prior Publication Data
US 2020/0330466 A1    Oct. 22, 2020

(30) Foreign Application Priority Data
Nov. 14, 2017   (IT) .................. 102017000130030

(51) Int. Cl.
*C07D 413/12*   (2006.01)
*A61K 31/513*   (2006.01)

(52) U.S. Cl.
CPC .......... *A61K 31/513* (2013.01); *C07D 413/12* (2013.01)

(58) Field of Classification Search
CPC ........................ C07D 413/12; A61K 31/513
See application file for complete search history.

(56) References Cited

U.S. PATENT DOCUMENTS

| 7,169,780 B2 | 1/2007 | Crescenzi et al. |
| 7,754,731 B2 | 7/2010 | Belyk et al. |
| 8,686,141 B2 | 4/2014 | Humphrey et al. |
| 10,259,778 B2 | 4/2019 | Budidet et al. |

FOREIGN PATENT DOCUMENTS

WO    2016/075605 A1   5/2016

OTHER PUBLICATIONS

Humphrey et al. "Development of a Second-Generation, Highly Efficient Manufacturing Route for the HIV Integrase Inhibitor Raltegravir Potassium" Org. Process Res. Dev. 2011, 15, 73-83. (Year: 2011).*

Humphrey et al., "Development of a Second-Generation, Highly Efficient Manufacturing Route for the HIV Integrase Inhibitor Raltegravir Potassium", Organic Process Research & Development, 2011, pp. 73-83, vol. 15, XP002782943.

International Search Report and Written Opinion, dated Feb. 2, 2019, from corresponding PCT application No. PCT/EP2018/081042.

* cited by examiner

*Primary Examiner* — Amanda L. Aguirre
(74) *Attorney, Agent, or Firm* — Nixon & Vanderhye

(57) ABSTRACT

Disclosed is a process for the preparation of Raltegravir and pharmaceutically acceptable salts thereof.

20 Claims, 8 Drawing Sheets

PROCESS FOR THE PREPARATION OF RALTEGRAVIR

TECHNICAL FIELD OF THE INVENTION

The present invention is related to a process for the preparation of highly pure Raltegravir and pharmaceutically acceptable salts thereof.

BACKGROUND OF THE INVENTION

Raltegravir is a compound of formula (I), chemically known as N-[2-[4-[(4-fluorophenyl)methylcarbamoyl]-5-hydroxy-1-methyl-6-oxopyrimidin-2-yl]propan-2-yl]-5-methyl-1,3,4-oxadiazole-2-carboxamide, and is an antiretroviral drug used to treat HIV infection. Raltegravir blocks the integrase, an HIV enzyme, which is responsible for the introduction of the genetic material of the virus in human chromosomes; this is a critical step in the pathogenesis of HIV infection. Raltegravir is usually marketed as a potassium salt under the brand name Isentress™

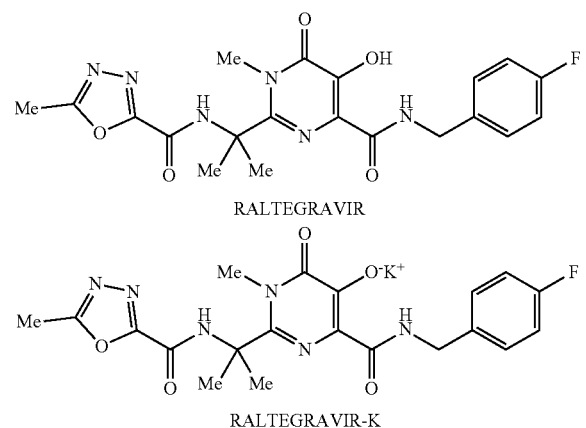

Raltegravir is described in U.S. Pat. No. 7,169,780 which discloses in general terms also a method for preparing Raltegravir comprising the reaction of 2-(1-amino-1-methylethyl)-N-(4-fluorobenzyl-5-hydroxy-1-methyl-6-oxo-1,6-dihydropyrimidine-4-carboxamide (II) with 2-[5-methyl-1,3,4-oxadiazolyl]carboxylic acid, in the presence of oxalyl chloride and trimethylamine in anhydrous DMF (Scheme 1). Actually, in Example 19 of the aforementioned patent, a solution of 2-[5-methyl-1,3,4-oxadiazolyl]carboxylic acid, which is a scarcely stable compound, is treated with 1.9 equivalents of oxalyl chloride in the presence of a few drops of anhydrous DMF; after reacting for 1 h the mixture is concentrated and the residue is triturated with n-hexane, then added to an equimolar solution of the compound (II) in acetonitrile, subsequently treated with 3 equivalents of triethylamine and maintained under stirring at room temperature overnight. Yield and purity of the product are not indicated, and the product is then isolated by preparative RP HPLC. Clearly this procedure is not suitable for commercial purposes.

Scheme 1

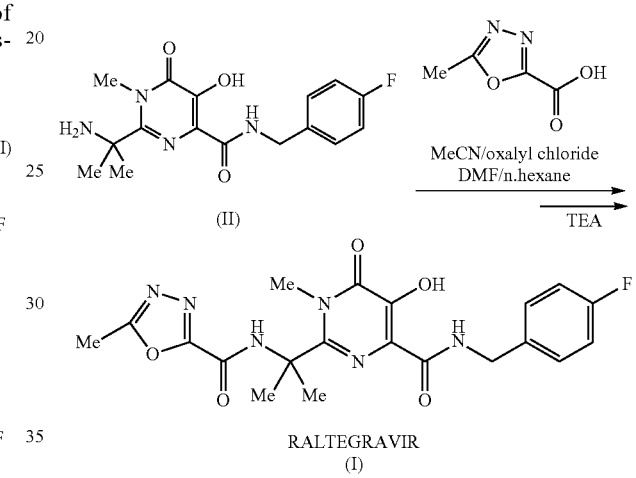

In U.S. Pat. No. 7,754,731, Example 1 part B, 2-[5-methyl-1,3,4-oxadiazolyl]carboxylic acid potassium salt in acetonitrile in the presence of a catalytic amount of DMF is treated at low temperature with oxalyl chloride and the resulting product (III, X=Cl), as suspension, is slowly added to a mixture of the anhydrous product (II) in N-methylmorpholine (NMM) and THF, maintaining the temperature ≤+5° C. (molar ratio III/II>2) until the disappearance of the product (II) is observed (Scheme 2).

Scheme 2

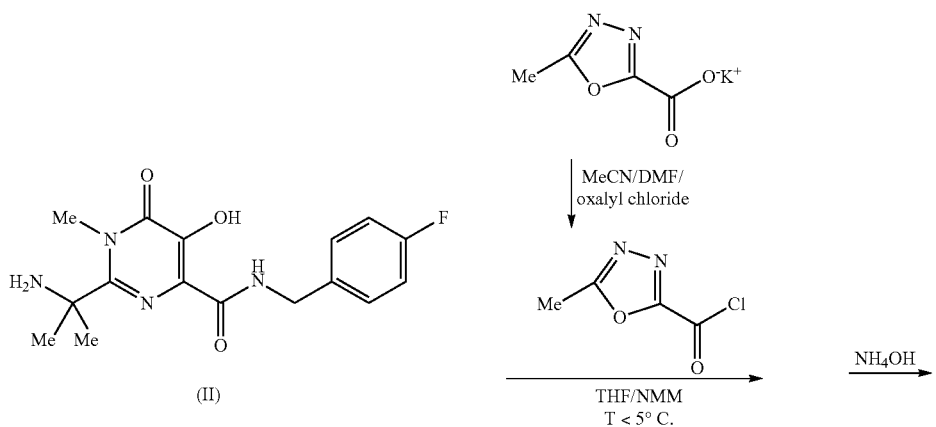

-continued

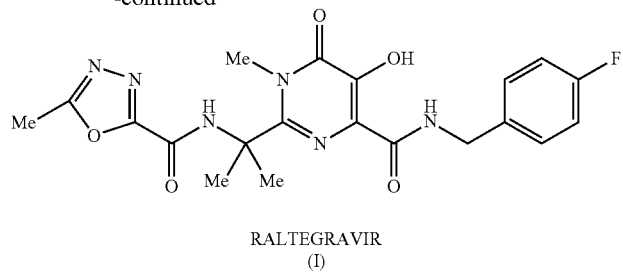

RALTEGRAVIR
(I)

The reaction mixture is then treated with an ammonium hydrate solution at a low temperature. The crystallization of the product (I) occurs after acidification of the mixture at pH 2-3, treatment with i-propyl alcohol and partial concentration at reduced pressure. By addition of water, the precipitation is completed; finally, after maturation of the mixture, the product is filtered, washed in sequence with water, with methanol and again with water, and finally dried under vacuum in a stream of nitrogen to give Raltegravir (91% yield); however the chemical purity of the product is not indicated.

The main disadvantage of this process is that it requires more than 2 equivalents of acylating agent, which is an expensive reagent, for the completion of the acylation stage; then a bisacylated product is formed in the mixture, on —$NH_2$ group as well as on —OH group, which therefore requires a subsequent low temperature selective hydrolysis of the -acyl group in a basic medium to release OH group after acidic treatment. Thus this process is expensive and produces large amounts of waste water; therefore it is not suitable for a large-scale production.

Later in U.S. Pat. No. 8,686,141 and in the corresponding publication [Organic Process Research & Development 2011, 15, 73-83], in order to overcome the problem of non-selective acylation and to reduce the use of at least 2.2 equivalents of the expensive oxadiazol derivative, after in-depth studies, the use of a derivative of the compound of formula (II) having the protected —OH group as the corresponding pivaloyl ester was proposed so as to use about 1.1 equivalents of (III) (where X=Cl), as reported in Scheme 3, working at low temperature both during the reaction and in the subsequent phase of removal of the protective group. A further advantage of the use of pivaloyl derivative of compound (II) is that this can be easily obtained in anhydrous form, thus avoiding the need of an expensive anhydrification process (II).

Scheme 3

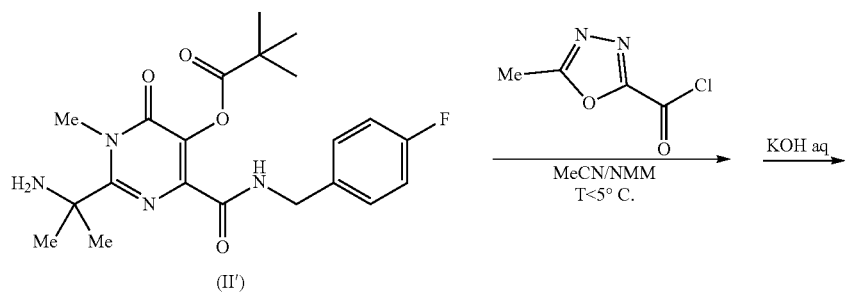

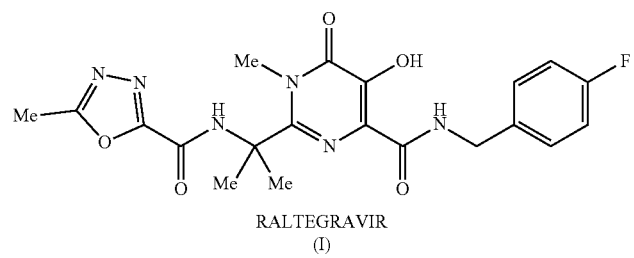

RALTEGRAVIR
(I)

Although this new process is more advantageous than the previous one, it still produces a large amount of wastewater and the introduction of a protective group which has to be subsequently removed is still necessary, thus reducing the sustainability of the process.

The same applies to the most recent patent application WO 2016/075605 where a similar process is used and where the OH protective group is a silyl derivative.

Therefore, there remains the need to provide an even more sustainable process suitable for industrial scale, with less wastewater, which avoids the need of using protective groups and at the same time allows to obtain the compound of formula (I) in high yield and chemical purity.

SUMMARY OF THE INVENTION

Figure 1:
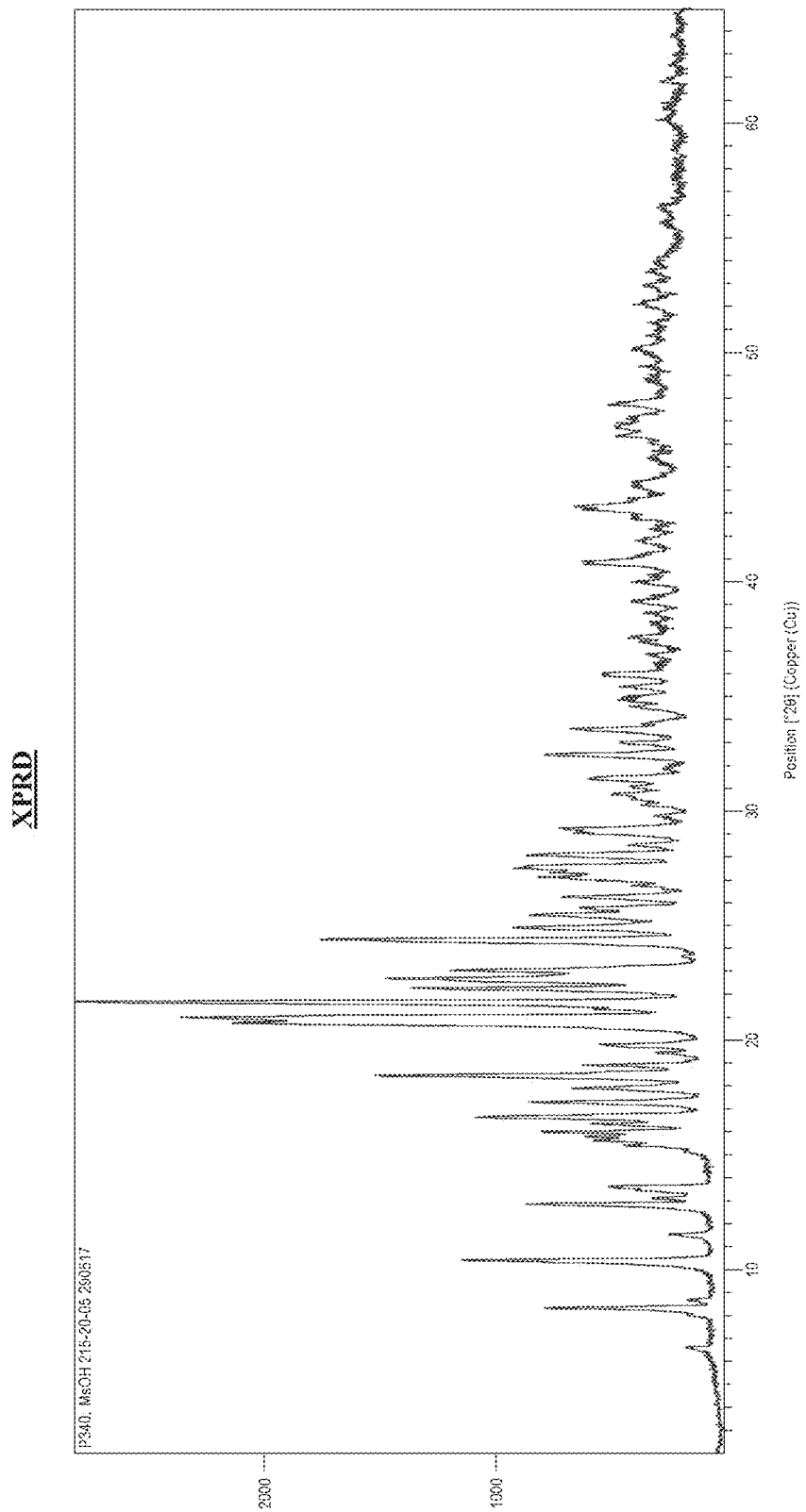
FIG. 1 shows the XRPD spectrum of the methanesulfonate salt of compound (II).

The present invention relates to a process for the preparation of Raltegravir of formula (I) or pharmaceutically acceptable salts thereof,

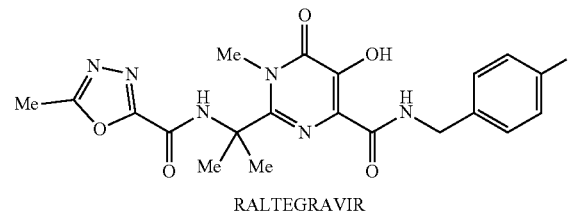

RALTEGRAVIR comprising the reaction of compound (II), which is not protected and in an anhydrous form, or of an anhydrous salt thereof,

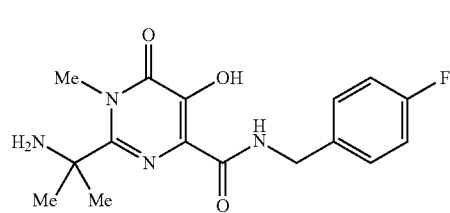

with a compound of formula (III),

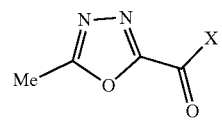

wherein

X=Cl; or

X=OAr wherein Ar is a phenyl group substituted with one or more groups, being the same or different from each other, selected from halogen (F, Cl, Br or I), cyano or nitro group; or X is a substituent of formula (IV):

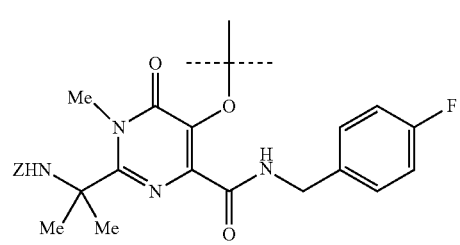

wherein Z=H (X=IVa) or Z=

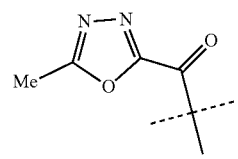

(X=IVb)

wherein compound (III) is used in an amount of from 1.1 to 1.3 molar equivalent with respect to compound (II);

in a reaction solvent and in the presence of one or more bases, wherein at least one of said bases has a pKa value ≥7.4, in a total amount of from 1.5 to 2.9 molar equivalent with respect to the compound of formula (II) or in total amount of from 2.5 to 3.9 molar equivalent with respect to the anhydrous salt of the compound of formula (II) which is produced in situ; and at a reaction temperature ranging from 45 to 75° C.

The invention also refers to the compounds of formula (IIa), (IIb) o (IIb),

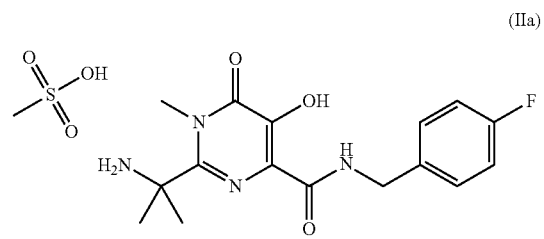

-continued

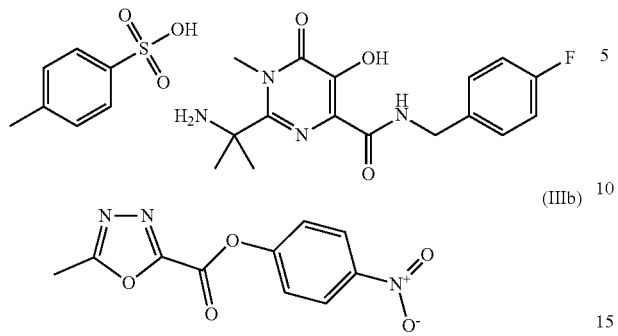

and their use in a process for the preparation of raltegravir of formula (I), or salts thereof.

DETAILED DESCRIPTION OF THE INVENTION

The present invention provides an alternative, improved and sustainable method for producing Raltegravir of formula (I) and its pharmaceutically acceptable salts, and in particular its potassium salt, having high chemical purity and excellent yield, surprisingly without requiring the use of protective groups or an excess of reagents as in the processes previously described in the state of the art.

The process of the present invention allows to have less amount of wastewater and to control the content of unwanted by-products by operating in the suitable conditions found by the inventors for the reaction of compound (II) with compound (III).

Object of the present invention is a process for the preparation of Raltegravir of formula (I), or pharmaceutically salts thereof.

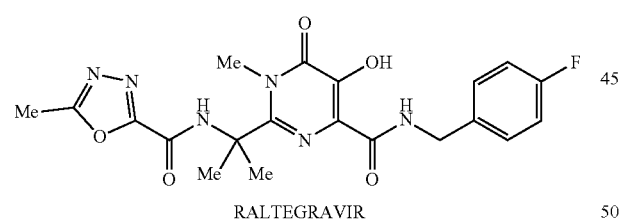

RALTEGRAVIR comprising the reaction of a compound of formula (II), which is not protected and in anhydrous form, or of an unprotected anhydrous salt thereof,

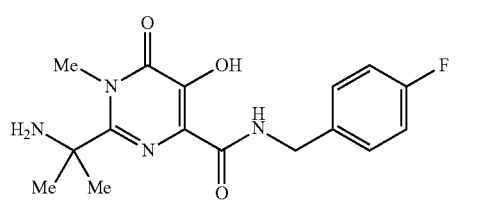

with a compound of formula (III),

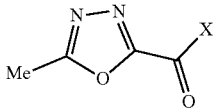

wherein X=Cl; or

X=OAr wherein Ar is a phenyl substituted with one or more groups, being the same or different from each other, selected from halogen (F, Cl, Br or I), cyano or nitro group, preferably selected from 2-chloro-4-nitrophenol, 2,3,4,5,6-pentafluorophenol, 4-nitrophenol, 4-cyanophenol, 3-nitrophenol, 3-chlorophenol, 4-bromophenol; or X is a substituent of formula (IV):

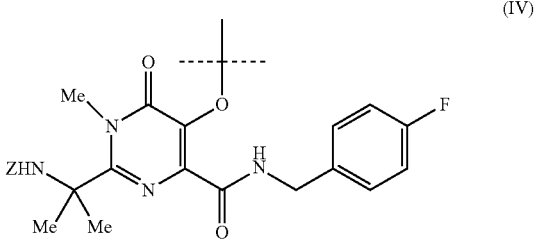

wherein Z=H (X=IVa) or Z=

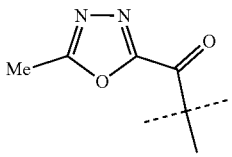

(X=IVb)

preferably X=Cl or 4-nitrophenol;

wherein the compound of formula (III) is used in amounts of from 1.1 to 1.3 molar equivalent with respect to compound of formula (II);

in a reaction solvent and in the presence of one or more bases, wherein at least one base has a pKa value ≥7.4, preferably between 7.4 and 12, more preferably between 8.5 and 11.5, in a total amount between 1.5 and 2.9 molar equivalent with respect to the compound of formula (II) or in a total amount between 2.5 and 3.9 molar equivalent with respect to the anhydrous salt of the compound of formula (II) which is released in situ; and at a reaction temperature between 45 and 75° C., preferably between 55° C. and 65° C. or more preferably between 50° C. and 60° C.

Raltegravir salt of formula (I) is preferably the potassium salt.

Preferably the anhydrous salt of a compound of formula (II) is the methanesulfonate salt of formula (IIa)

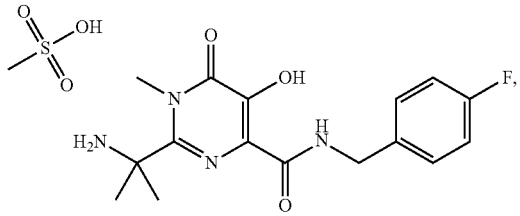

(IIa)

or p-toluenesulfonate of formula (IIb)

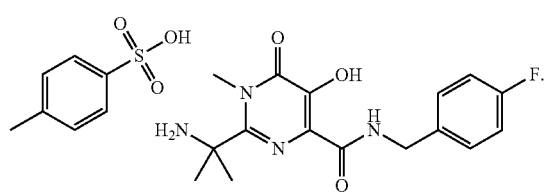

(IIb)

In the state of the art compound (III), where X is the substituent of formula (IVb), was considered an undesirable by-product of the reaction and had to be further hydrolysed to provide the desired final product Raltegravir of formula (I).

It has surprisingly been found that under the particular conditions of the present invention, said intermediate may be used directly as an acylating agent to give the desired product and allowing to reduce the excess of acylating agent of formula (III) where X=Cl, otherwise necessary in the state of the art to obtain Raltegravir of formula (I).

According to the present invention, the expression "base having a value of pKa ≥7.4" means a base having at least one value of pKa ≥7.4. The Applicant refers to pKa values reported in the text: D. R. Lide, Handbook of Chemistry and Physics, 83rd ed. 2002-2003, section 8-46/56; Internet link: https://labs.chem.ucsb.edu/zhang/liming/pdf/pKas_of_Organic_Acids_and_Bases.pdf The base having a value of pKa ≥7.4 may have the general formula

NR₁R₂R₃ (VI), wherein R₁, R₂ and R₃, being the same or different from each other, may be a straight or branched C₁-C₈ alkyl group, optionally substituted by alkoxy, dialkylamino or phenyl groups; or one of R₁, R₂ and R₃ may be an aromatic heterocyclic ring; R₁ and R₂ taken together may form a non-aromatic heterocyclic ring with the nitrogen atom. The base is preferably selected, for Example, from tetramethylethylenediamine, triethylamine, diisopropylethylamine, 4-dimethylaminopyridine.

The reaction solvent is preferably selected from acetonitrile, toluene or mixtures thereof.

The unprotected compound of formula (II), in anhydrous form, can be obtained according to methods known in the art or it can preferably be generated in situ by a basic treatment of an appropriate anhydrous salt thereof.

An anhydrous salt of the compound (II), which is preferably methanesulfonate or p-toluenesulfonate, can be obtained, for Example according to the procedure reported in Scheme 4, starting from a compound of formula (V), in which Cbz is a carbobenzyloxy group, obtained by known techniques, by hydrogenation in the presence of a heterogeneous palladium catalyst and an equivalent of RSO₃H acid in aqueous methanol; and the subsequent precipitation, after removal of the catalyst from the reaction mixture, through treatment with i-PrOH:

Scheme 4

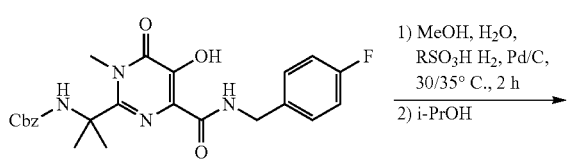

(V)

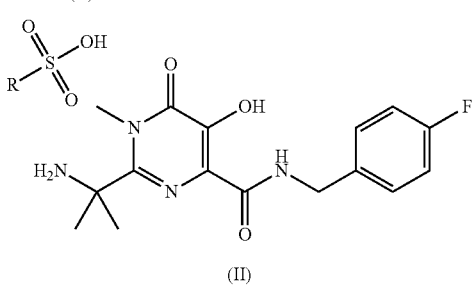

(II)

anhydrous metanesulfonate of p-toluensulfonate wherein R is preferably methyl or p-tolyl.

The anhydrous salt of compound (II), after drying, can be used as such in the process for the preparation of Raltegravir of formula (I), providing in situ the compound of formula (II) by treatment with a base in the subsequent reaction.

In a preferred embodiment of the present invention, the process for the preparation of Raltegravir of formula (I), or pharmaceutically acceptable salts thereof,

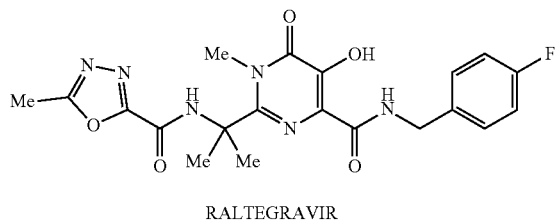

(I)

RALTEGRAVIR comprises the reaction of a compound of formula (IIa) or (IIb)

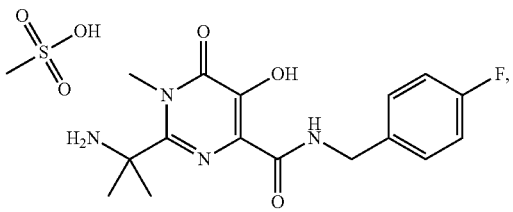

(IIa)

-continued

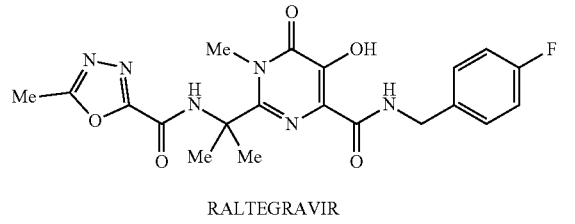
(IIb)

with a compound of formula (III),

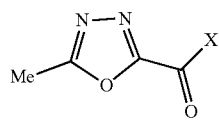
(III)

where X is as defined above.

According to a further preferred embodiment of the present invention, the process for the preparation of Raltegravir of formula (I), or pharmaceutically acceptable salts thereof,

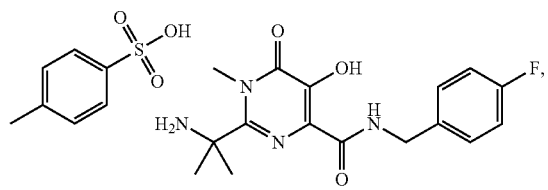
(I)

RALTEGRAVIR comprises the reaction of a compound of formula (IIa) or (IIb)

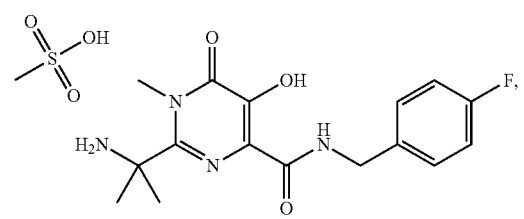
(IIa)

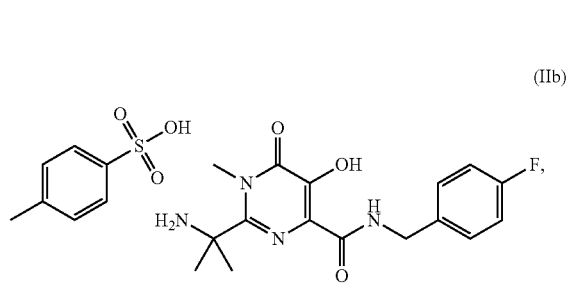
(IIb)

with a compound of formula (IIIa),

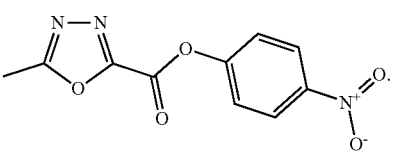
(IIIa)

According to a further preferred embodiment of the invention, the process for the preparation of Raltegravir having formula (I), or pharmaceutically acceptable salts thereof,

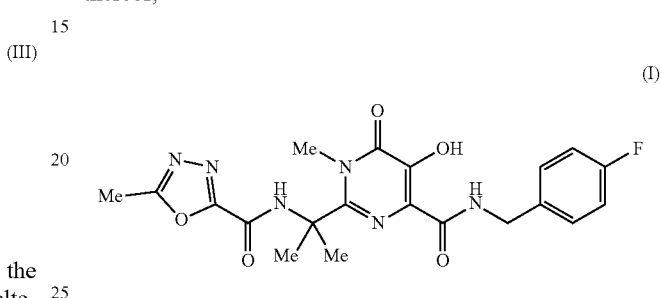
(I)

RALTEGRAVIR comprises the reaction of a compound of formula (IIa) or (IIb)

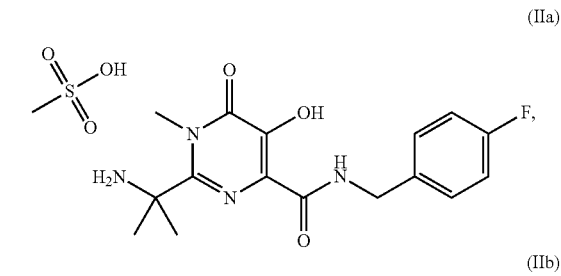
(IIa)

(IIb)

with a compound of formula (IIb), (IIIb)

Further objects of the present invention are the anhydrous methanesulfonate salt of the compound of formula (IIa) and the anhydrous p-toluenesulfonate salt of the compound of formula (IIb), as well as the 4-nitrophenoxy ester of 2-[5-methyl-1,3,4-oxadiazolyl] carboxylic acid of formula (IIb)

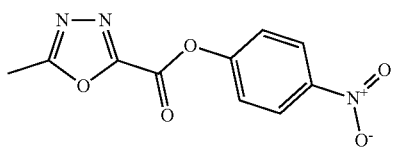 [SMILES: Cc1nnc(C(=O)Oc2ccc([N+](=O)[O-])cc2)o1]

which can be used as intermediates in the preparation of Raltegravir of formula (I).

According to a further aspect of the present invention, the compound (III, X=Cl) can be prepared by treating the potassium salt of 2-[5-methyl-1,3,4-oxadiazolyl]carboxylic acid in a solvent or mixture of solvents, such as for Example acetonitrile or toluene, at low temperature with oxalyl chloride in the presence of a catalytic amount of DMF and subsequently partially concentrating the mixture under reduced pressure. The mixture thus obtained can therefore be used as such in the process for the preparation of Raltegravir of formula (I).

Alternatively, the compound (III, X=Cl) is transformed into the corresponding new derivative (III, X=OAr), according to the present invention as described in the Examples hereinafter, before being used in the process for the preparation of Raltegravir of formula (I).

According to a preferred embodiment, the compound of formula (II) in the unprotected form, anhydrous, or preferably in the form of an anhydrous salt thereof, more preferably in the form of the corresponding anhydrous methanesulfonate salt, is suspended in a solvent, preferably acetonitrile, and treated with one or more bases, wherein at least one of which has a value of pKa ≥7.4, preferably a pKa value between 7.4 and 12, more preferably between 8.5 and 11.5, in a total amount between 1.5 and 2.9 molar equivalent with respect to the compound of formula (II) or in a total amount between 2.5 and 3.9 molar equivalent with respect to the anhydrous salt of the compound of formula (II) which is formed in situ. To this mixture the compound of formula (III), as defined above, diluted in a reaction solvent, such as for Example acetonitrile or toluene, is slowly added at a temperature between 45° and 75° C., preferably between 55° and 65° C. or more preferably at a temperature between 500 and 60° C.; finally, the reaction mixture is maintained under stirring at a temperature between 45° and 75° C., preferably between 55° C. and 65° C., more preferably at a temperature between 50° and 60° C., until the complete consumption of compound of formula (II). The mixture is then treated with water and acetic acid up to pH of 4.0-4.5 at room temperature and subsequently with ethyl acetate; the separated organic phase is concentrated and the residue crystallized from ethanol or from a mixture of ethanol acetonitrile 98/2 to provide Raltegravir of formula (I) with HPLC purity greater than 99.5%, preferably ≥99.8% and with a content of each individual impurity ≤0.06%.

According to a particularly preferred aspect of the invention, the process for the preparation of Raltegravir of formula (I) is carried out as shown in Scheme 5, wherein the anhydrous salt of the compound of formula (II) is the corresponding methanesulfonate, which is reacted with 1.1-1.3 equivalents of compound (III, X=Cl), in the presence of 2.5-3.9 equivalents of triethylamine in a reaction solvent (which is acetonitrile or toluene or a mixture thereof) at a temperature between 50 and 60° C. When the reaction is complete and after the subsequent work-up according to known methods, the product is isolated from ethanol.

Scheme 5

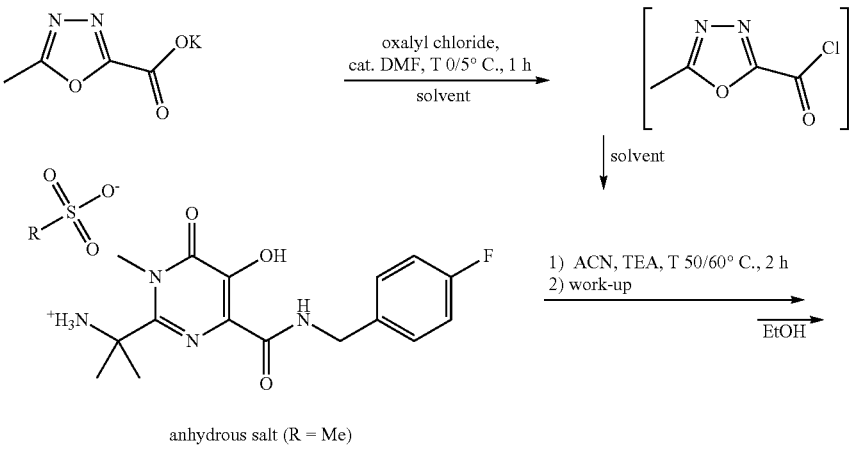

anhydrous salt (R = Me)

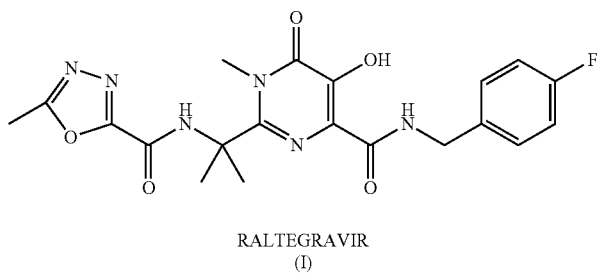

RALTEGRAVIR
(I)

Raltegravir of formula (I), obtained with the process of the present invention, can then be converted into its pharmacologically acceptable salts, and in particular in its potassium salt, by methods known in the art.

Raltegravir of formula (I) is thus obtainable in high yield (88-95%) and high chemical purity (≥99.5%) as demonstrated by HPLC analysis.

A final aspect of the present invention is the use of new anhydrous salts of the compound of formula (II) and of the compounds of formula (III).

The following Examples further illustrate the invention.

Analytical Methods

X-ray diffractometric analysis—powder method (XRPD)

The samples, before being analyzed, were subjected to a light grinding in an agate mortar and then analyzed by X-ray diffractometry (powder method—XRPD), having the following instrumental characteristics:

Philips PW1800/10 diffractometer
X'Pert High Score data processing software—v. 2.0a (PANalytical)
Cu Kα radiation (Kα$_1$=1.54060 Å Kα$_2$=1.54439 Å)
graphite monochromator
divergent automatic slide
generator power: 45 Kv, 35 mA
scanning interval: 2°-65° 2θ
scanning speed (step): 0.02° 2θ/sec
counting time per step: 1.0 sec
Samples are analyzed in the scan interval: 2°-65° 2θ.

DSC Analysis (Differential Scanning Calorimetry)

The DSC analyses were conducted using METTLER TOLEDO DSC 822e instrument. The experiments were conducted with a heating ramp of 10.0° C./min in the range of 30°-350° C. and with a nitrogen flow of 40 ml/min. 40 μL aluminum crucibles with perforated lid were used.

IR Analysis (Infrared Spectroscopy)

IR spectra were recorded using JASCO FT-IR 460 Plus spectrophotometer. The samples were prepared by grinding about 5 mg of sample with approximately 500 mg of KBr and analyzed in the range of 4000-400 cm$^{-1}$ with a resolution of 4 cm$^{-1}$.

NMR (Nuclear Magnetic Resonance) Analysis

NMR analyses were performed using a Bruker Avance 300 MHz instrument

Example 1—Preparation of Methanesulfonate Salt of the Compound of Formula (II)

40 g (85.4 mmol) of benzyl-(2-(4-((4-fluorobenzyl)carbamoyl)-5-hydroxy-1-methyl-6-oxo-1,6-dihydropyrimidin-2-yl)propan-2-yl)-carbamate, 83.7 g (87.1 mmol) of methanesulfonic acid, 0.8 g of 5% Pd/C (50% humidity) were loaded in a 1 L autoclave with 180 mL of aqueous methanol (8:1). After 3 cycles of vacuum-hydrogen, the autoclave was pressurized with 1 bar of hydrogen and the mixture was heated to 40° C. until the carbobenzyloxy group was completely removed. After filtration of the catalyst, the mixture was reduced to a small volume and recovered with 120 ml of isopropanol and concentrated again. The operation was repeated up to KF<1. Finally the isopropanol mixture was cooled and maintained under stirring at 0-5° C. for 1 h. The solid was filtered, dried under vacuum at 60° C. to give 34.9 g of the compound of formula (II) in the form of methanesulphonate with a 94.9% yield. The product was characterized by X-ray (FIG. 1).

Figure 2:
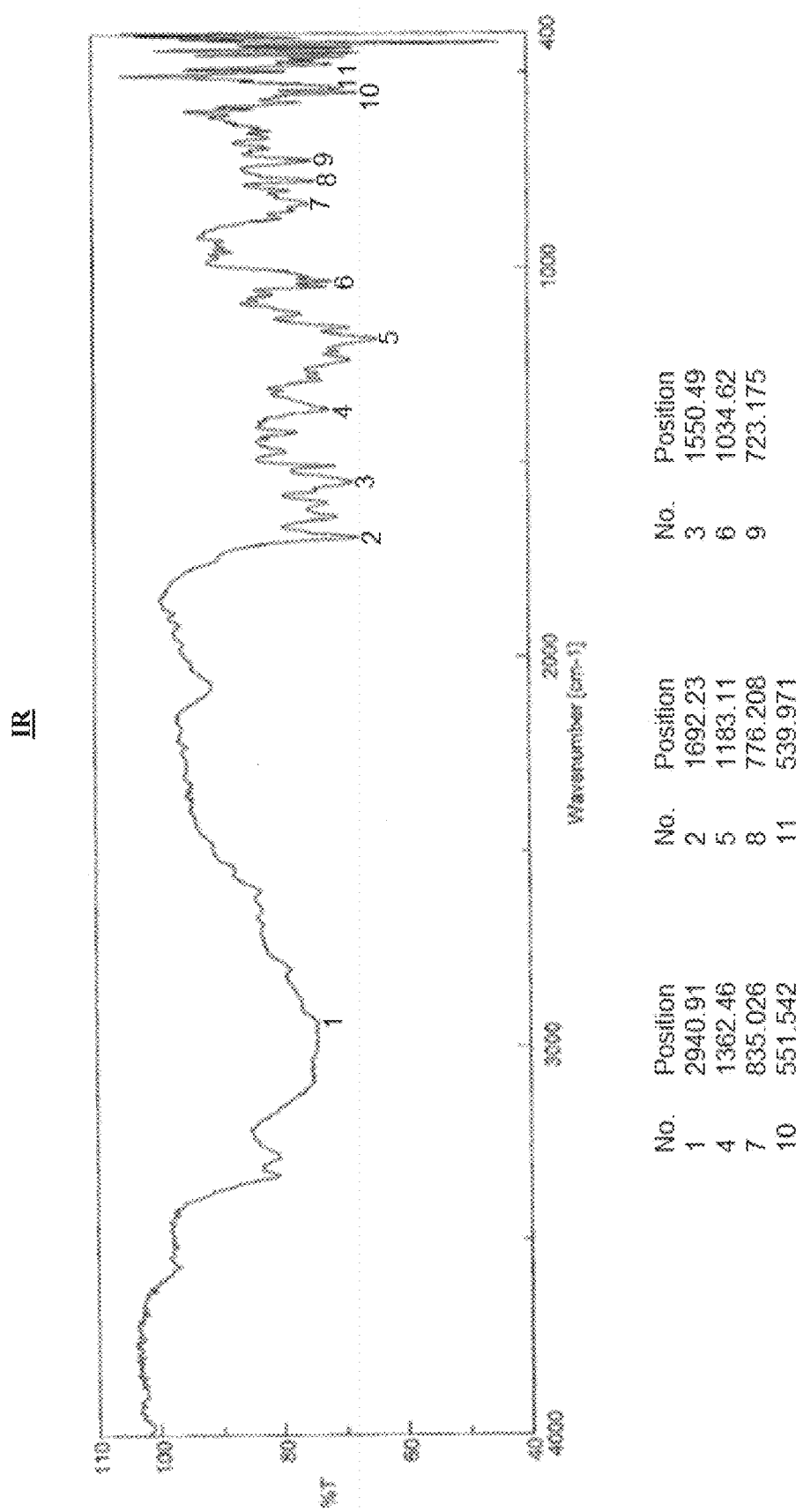
FIG. 2 shows the IR spectrum of the methanesulfonate salt of compound (II).
Figure 3:
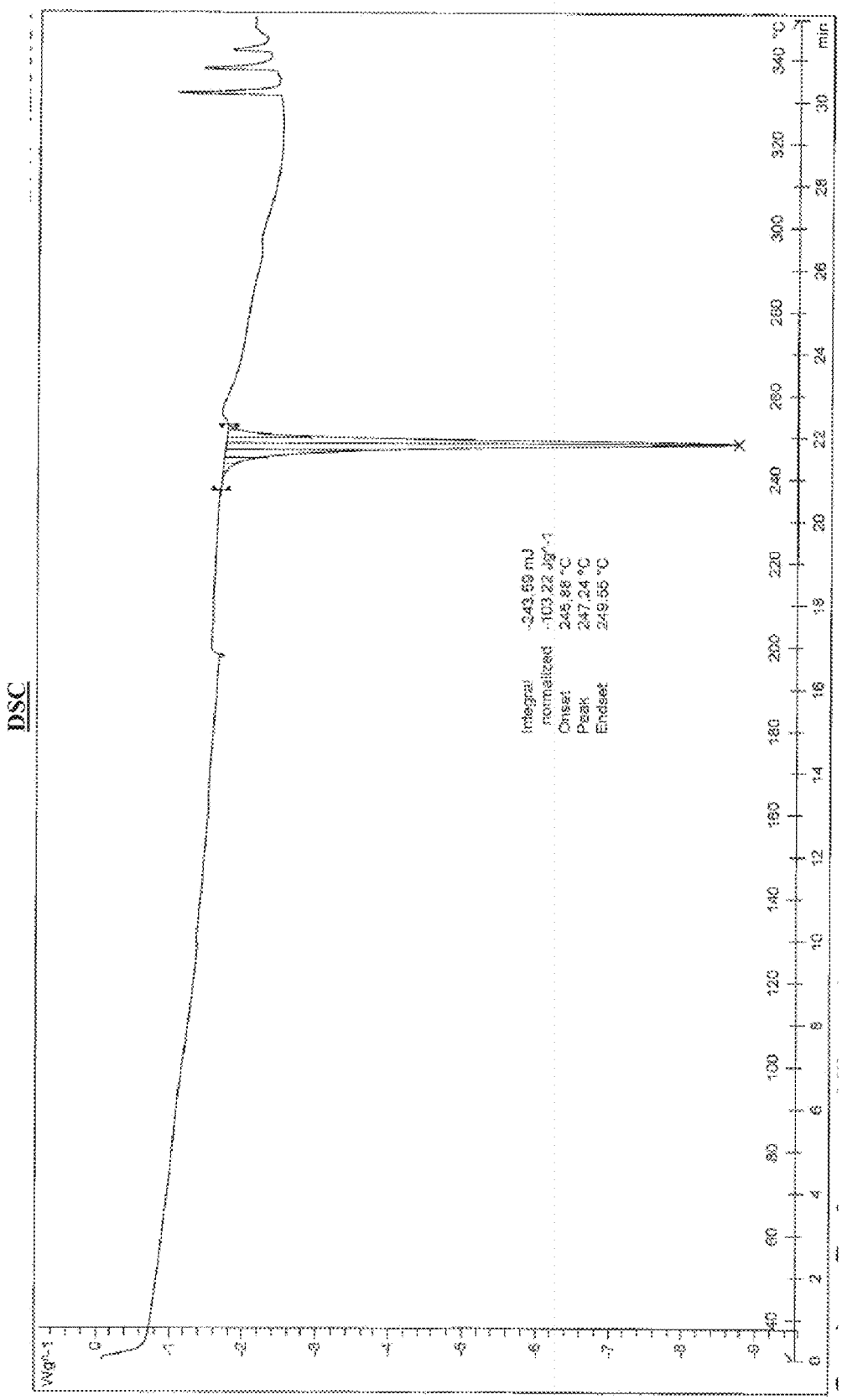
FIG. 3 shows the DSC curve of the methanesulfonate salt of compound (II).

IR (FIG. 2), DSC (FIG. 3) and NMR as below reported.

$^1$H-NMR (DMSO d$_6$, 300 MHz) (δ in ppm with respect to TMS): 1.74 (6H, s, —CH$_3$-E); 2.41 (3H, s, CH$_3$SO$_3$H); 3.55 (3H, s, —NCH$_3$); 4.55 (2H, d, J=5.5 Hz, H—C); 7.18 (2H, t, J=9 Hz, H-A); 7.43 (2H, dd, J=9, 6 Hz, H—B); 8.54 (3H, broad, NH$_3^+$); 9.64 (1H, t, J=5.5 Hz, NH-D); 12.25 (1H, broad, OH).

$^{13}$C-NMR (DMSO d6, 300 MHz) (δ in ppm with respect to TMS, the multiplicity was obtained from the spectrum DEPT-135): 23.9 (CH$_3$-E); 33.3 (—NCH$_3$); 39.7 (CH$_3$SO$_3$H); 41.3 (CH$_2$—C); 57.3; 115.1 (d, J=22 Hz, CH-A); 123.7; 129.6 (d, J=8 Hz, CH—B); 134.5 (d, J=3 Hz); 146.6; 149.4; 158.4; 159.7 e 162.9 (d, J$_{C-F}$=240 Hz); 168.0.

| XPRD Peak List: | |
|---|---|
| Pos. [°2θ] | d-spacing [Å] |
| 6.6193 | 13.35360 |
| 8.3487 | 10.59105 |
| 8.6639 | 10.20643 |
| 10.4091 | 8.49880 |
| 11.5387 | 7.66918 |
| 12.8626 | 6.88266 |
| 13.1079 | 6.75441 |
| 13.6368 | 6.49358 |
| 15.4072 | 5.75120 |
| 15.6252 | 5.67142 |
| 15.7929 | 5.61159 |
| 15.9938 | 5.54156 |
| 16.3400 | 5.42491 |
| 16.6467 | 5.32565 |
| 17.2937 | 5.12784 |
| 17.9142 | 4.95158 |
| 18.4556 | 4.80753 |
| 18.9134 | 4.69220 |
| 19.4603 | 4.56155 |
| 19.8168 | 4.48027 |
| 20.7460 | 4.28165 |
| 21.0420 | 4.22209 |
| 21.3439 | 4.16305 |
| 21.7021 | 4.09515 |
| 22.2674 | 3.99245 |
| 22.6912 | 3.91882 |
| 23.0435 | 3.85971 |
| 24.4112 | 3.64647 |
| 24.9157 | 3.57376 |
| 25.4834 | 3.49543 |
| 25.8025 | 3.45291 |
| 26.2566 | 3.39422 |
| 26.7516 | 3.33253 |
| 27.1301 | 3.28689 |
| 27.6477 | 3.22652 |
| 28.1348 | 3.17175 |
| 28.5289 | 3.12883 |
| 29.0269 | 3.07627 |
| 29.2816 | 3.05009 |
| 29.8239 | 2.99586 |
| 30.2673 | 2.95297 |
| 30.7530 | 2.90743 |
| 31.4546 | 2.84417 |
| 32.5117 | 2.75407 |
| 33.0130 | 2.71338 |
| 33.5874 | 2.66828 |
| 34.5395 | 2.59688 |
| 34.8425 | 2.57499 |
| 35.4381 | 2.53306 |
| 35.9699 | 2.49682 |
| 36.8181 | 2.44123 |
| 37.6031 | 2.39205 |
| 38.6259 | 2.33103 |
| 39.1166 | 2.30291 |
| 39.9613 | 2.25617 |

Example 2—Preparation of p-toluenesulfonate of 2-(2-aminoprop-2-yl)-N-(4-fluorobenzyl)-5-hydroxy-1-methyl-6-oxo-1,6-dihydropyrimidine-4-carboxamide (II)

Figure 4:
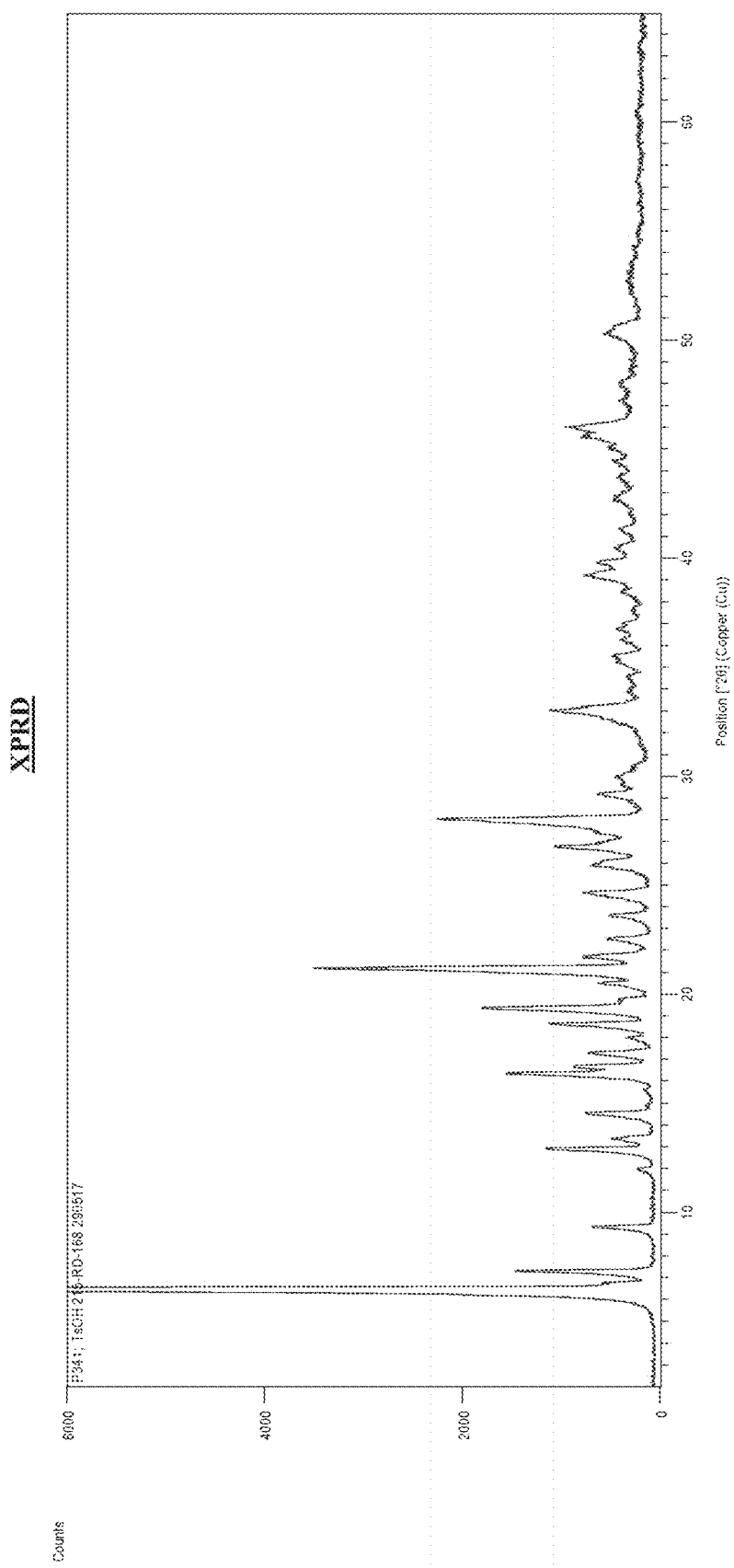
FIG. 4 shows the XRPD spectrum of the p-toluenesulfonate salt of compound (II).
Figure 5:
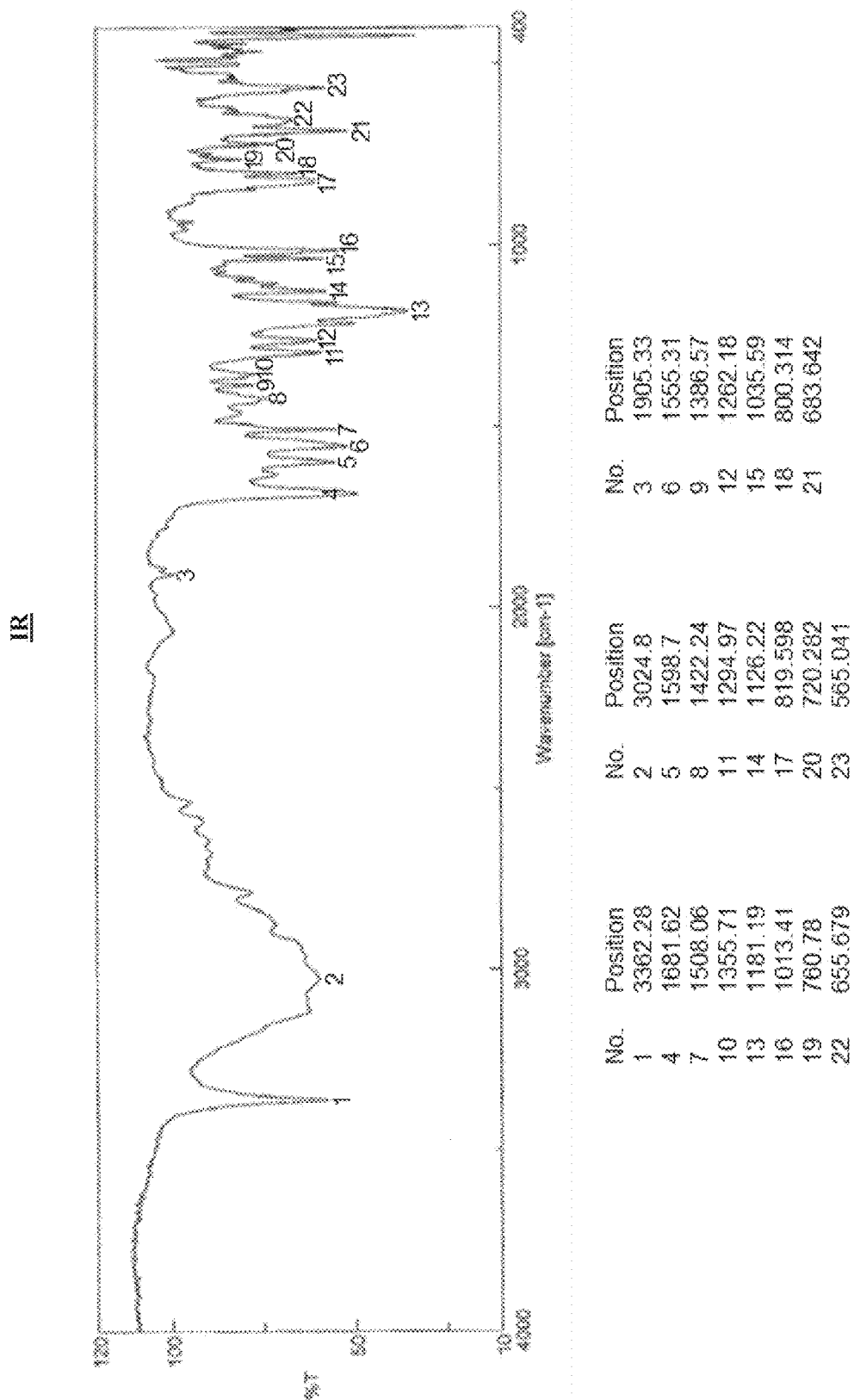
FIG. 5 shows the IR spectrum of the p-toluenesulfonate salt of compound (II).
Figure 6:
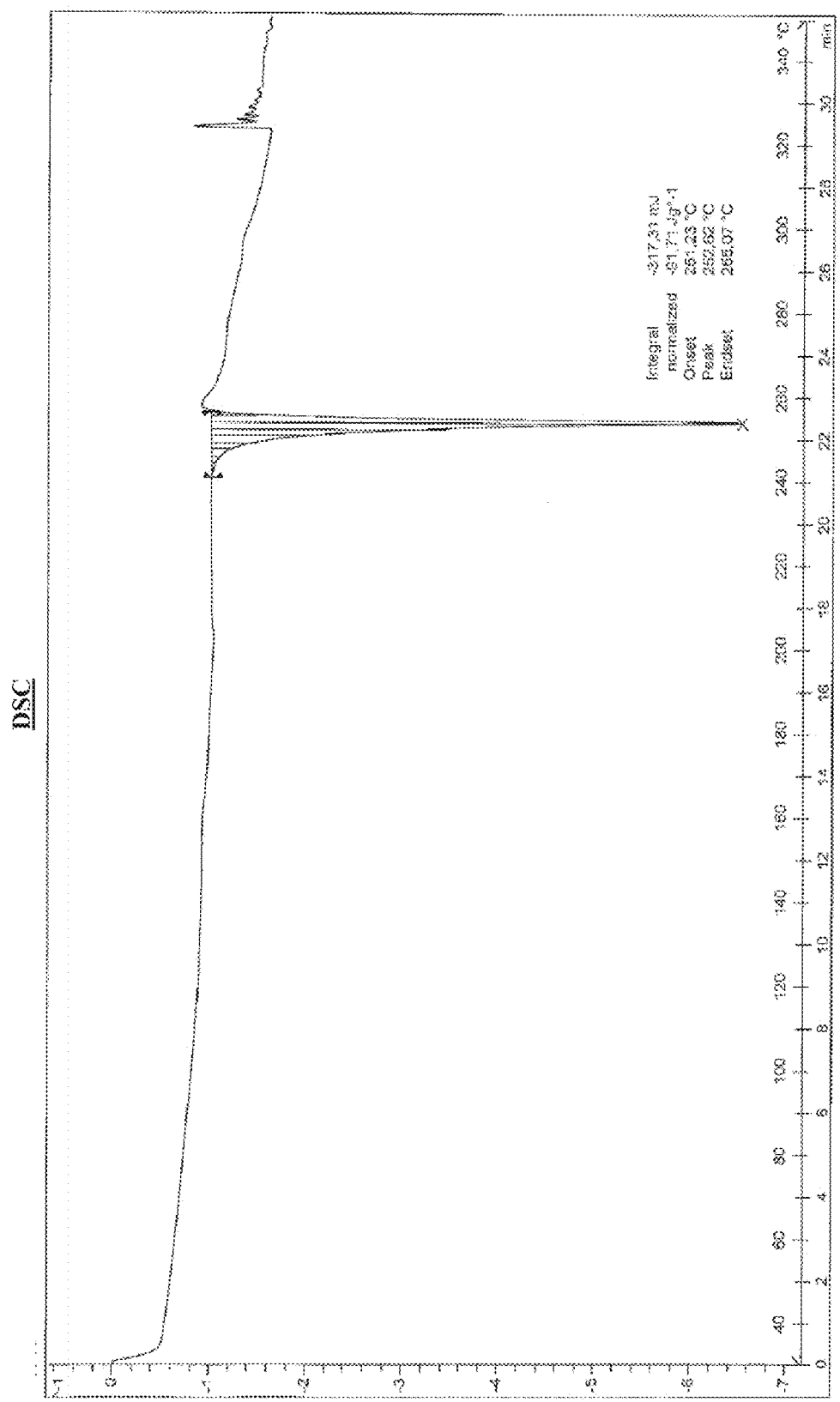
FIG. 6 shows the DSC curve of the p-toluenesulfonate salt of compound (II).

Operating as described in Example 1, but using 16.5 g (87.1 mmol) of p-toluenesulfonic acid mono hydrate, the compound of formula (II) was obtained in the form of para-toluenesulfonate (95.1% yield. The product was characterized by X-Rays (FIG. 4), IR (FIG. 5), DSC (FIG. 6) and NMR as reported below.

$^1$H-NMR (DMSO $d_6$, 300 MHz) (δ in ppm with respect to TMS): 1.73 (6H, s, —$CH_3$-E); 2.30 (3H, s, $CH_3$ TsOH); 3.55 (3H, s, —$NCH_3$); 4.52 (2H, d, J=5.5 Hz, H—C); 7.14 e 7.51 (4H, AA 'XX' system, J=8 Hz, TsOH); 7.18 (2H, t, J=9 Hz, H-A); 7.40 (2H, dd, J=9, 6 Hz, H—B); 8.50 (3H, broad, $NH_3^+$); 9.53 (1H, t, J=5.5 Hz, NH-D); 12.25 (1H, broad, OH).

$^{13}$C-NMR (DMSO d6, 300 MHz) (δ in ppm with respect to TMS, multiplicity was obtained from the spectrum DEPT-135): 20.8 ($CH_3$ TsOH); 23.9 ($CH_3$-E); 33.3 (—$NCH_3$); 41.3 ($CH_2$—C); 57.3; 115.1 (d, $J_{C-F}$=22 Hz, CH-A); 123.6; 125.4 (CH TsOH); 128.2 (CH TsOH); 129.5 (d, $J_{C-F}$=8 Hz, CH—B); 134.4 (d, J=3 Hz); 138.1; 145.0; 146.6; 149.4; 158.4; 159.7 e 162.9 (d, $J_{C-F}$=240 Hz); 168.0.

XPRD Peak List:

| Pos. [°2θ] | d-spacing [Å] |
|---|---|
| 6.5183 | 13.56046 |
| 6.7801 | 13.03735 |
| 7.3380 | 12.04737 |
| 9.3442 | 9.46478 |
| 11.9741 | 7.39130 |
| 12.9274 | 6.84830 |
| 13.3678 | 6.62365 |
| 14.5571 | 6.08506 |
| 16.3986 | 5.40565 |
| 16.6986 | 5.30919 |
| 17.3312 | 5.11683 |
| 18.0239 | 4.92170 |
| 18.6602 | 4.75528 |
| 19.4030 | 4.57488 |
| 19.7637 | 4.49220 |
| 20.5096 | 4.33048 |
| 21.2223 | 4.18663 |
| 21.7625 | 4.08391 |
| 22.5897 | 3.93620 |
| 23.5908 | 3.77138 |
| 24.6890 | 3.60607 |
| 25.8947 | 3.44083 |
| 26.1153 | 3.41226 |
| 26.7678 | 3.33055 |
| 28.0824 | 3.17756 |
| 29.1735 | 3.06115 |
| 29.9928 | 2.97937 |
| 33.0190 | 2.71290 |
| 33.9051 | 2.64400 |
| 34.5904 | 2.59317 |
| 35.5344 | 2.52642 |
| 36.2292 | 2.47955 |
| 36.7560 | 2.44521 |
| 37.6334 | 2.39019 |
| 38.4779 | 2.33965 |
| 39.2416 | 2.29587 |
| 39.8211 | 2.26378 |

Example 3—Preparation of Raltegravir

Under inert atmosphere, 31 g (187 mmol) of 5-methyl-1,3,4-oxadiazole-2-carboxylic acid potassium salt, 248 ml of toluene and 0.46 ml of DMF were loaded into a 1 L flask. To said mixture at a temperature of 0-5° C., 16.1 ml (190 mmol) of oxalyl chloride were slowly added and, after 1.5 h, under vacuum, toluene was partially concentrated up to about half of the initial volume, not exceeding the temperature of 60° C. Fresh toluene was added and the operation was repeated. The suspension containing 5-methyl-1,3,4-oxadiazole-2-carboxylic acid chloride salt (about 185 mmol) was cooled to 20° C., and slowly added by dripping to a mixture of 69 ml (497 mmol) of trimethylamine, 401 ml of acetonitrile and 67 g (155 moles) of methanesulphonate of compound (II), obtained as reported in Example 1. The mixture was maintained under stirring in a 2 L flask at a temperature of 50-55° C. until completion of the reaction and subsequently cooled to room temperature. The process was carried out by adding 120 ml of water, 40 ml of acetic acid and 400 ml of ethyl acetate to the obtained mixture; after separation of the lower phase, the organic phase was washed with water, which was discarded, and then concentrated to small volume. The residue was diluted with 480 ml of ethanol and concentrated under vacuum and crystallized from ethanol. 60 g (87% yield) of Raltegravir, having chemical purity ≥99.5% HPLC, were recovered after filtration at 5-10° C. and drying.

Example 4—Preparation of Raltegravir

Operating as described in Example 3, but using 2.6 molar equivalents with respect to the compound of formula (II) of different bases and 1.15 molar equivalents of acyl chloride, the results reported in Table 1 were obtained after the reaction was carried out for 3 hours

TABLE 1

| Amine | pKa | Area % (II) | Area % (V; bis-acylated) |
|---|---|---|---|
| Pyridine | 5.2 | 45.8 | 4.9 |
| N-methyl morpholine | 7.5 | 2.6 | 0.13 |
| N-methyl morpholine * | 7.5 | 3.3 | 0.06 |
| Tetramethylethylenediamine | 5.85/8.97 | 3 | 0.6 |
| Triethylamine | 10.7 | 0.5 | 0.02 |
| Triethylamine * | 10.7 | 0.3 | 0.02 |
| Diisopropylethylamine | 11.4 | 0.9 | 0.05 |

* 1.5 mol % of 4-dimethylaminopyridine (pKa 9.7) were added

Example 5—Preparation of Raltegravir Starting from the Compound of Formula (II) Free Base in Hydrated Form Operating as described in Example 1, but after the catalyst was filtered, NaOH 2M was slowly dripped to reach pH ~8 maintaining a temperature lower than 20° C., to the solution cooled to about 20° C. At completed addition, the product of formula (II) was precipitated in the form of free base, the suspension was maintained at 0°-5° C. for 1 hour, filtered and the solid washed with cold water (2×45 ml), dried in vacuum at 60° C. for at least 6 hours to give the compound of formula (II) free base in hydrated form (26.6 g, KF 4.74%) in 93.4% yield on anhydrous base.

A suspension hydrated form of the compound of formula (II) free base (21.3 g, 60.7 mmol) in in toluene (100 ml) was dried by complete distillation up to KF≤0.1%. Then the suspension was distilled to residue under vacuum and suspended again in acetonitrile (100 ml). Triethylamine (15.4 g, 152 mmol) was added to the suspension, the mixture was heated to 50°-60° C. and a suspension of the compound (III, X═Cl) (50 ml, 72.7 mmol) was dripped under nitrogen. The mixture was maintained at 50°-60° C. until completion of the reaction and subsequently cooled to room temperature. Water (45 ml), ethyl acetate (150 ml) and glacial acetic acid to pH 4-4.5 were added to the suspension. The organic phase recovered by decanting was washed again with water (45 ml) and subsequently concentrated. The suspension was then diluted with EtOH (130 ml), heated to 60°-70° C. for 1 h, cooled to 0°-5° C. and, after 1 h, filtered and washed with cold EtOH. The solid was dried under vacuum at 60° C. for at least 6 h to give Raltegravir (24.3 g, 54.6 mmol) in 90% yield and 99.8% HPLC purity.

Example 6—Preparation of Raltegravir Starting from the Compound of Formula (IVb)

In nitrogen atmosphere, a solution of the compound (III, X═Cl) (60 g, 48 mmol) in toluene, previously prepared according to the above reported Examples, was slowly dripped (in about 15 min.) maintaining a temperature of 0°-5° C. to a solution of methanesulphonate of the compound of formula (II) (8.6 g, 20 mmol) in acetonitrile (45 ml) and triethylamine (4.05 g, 40 mmol) cooled to 0°-5° C. After 1 h the suspension containing Raltegravir bis-acylate product (IVb) was slowly dripped to a methanesulphonate solution of the compound of formula (II) (8.6 g, 20 mmol) in acetonitrile (45 ml) and triethylamine (4.05 g, 40 mmol) previously heated to 50°-60° C. At addition complete, the suspension was maintained under stirring at 50°-60° C. until the reaction is complete. Water (25 ml) followed by glacial acetic acid up to pH 4-4.5 were added to the suspension cooled at 20°-25° C. Ethyl acetate (200 ml) was added to the obtained solution and the mixture was maintained under stirring for 15 min. at 20°-25° C. The organic phase was decanted and washed again with water (20 ml). After subsequent decanting, the organic phase was completely distilled under vacuum. The solid residue was suspended in ethanol (120 ml) and the suspension was heated to 60°-70° C. for at least 1 h, then cooled to 0°-5° C. After 1 h the solid was filtered and washed with cold ethanol (2×20 ml), dried under vacuum at 60° C. for at least 6 h to give Raltegravir (16 g, 36 mmol) in 90% yield and HPLC purity of 99.7%.

Example 7—Preparation of Raltegravir Starting from the Compound of Formula (III) (where X═4-Nitrophenoxy) (IIIb)

Figure 7:
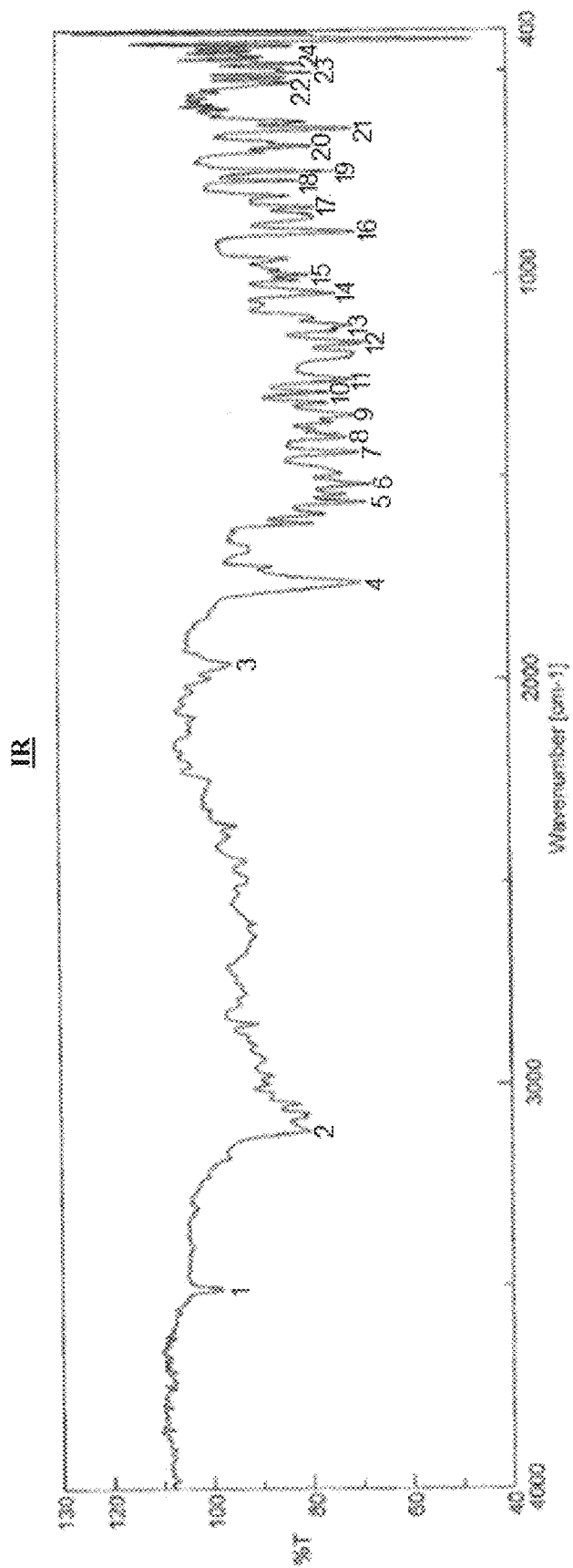
FIG. 7 shows the IR spectrum of compound (IIIb).
Figure 8:
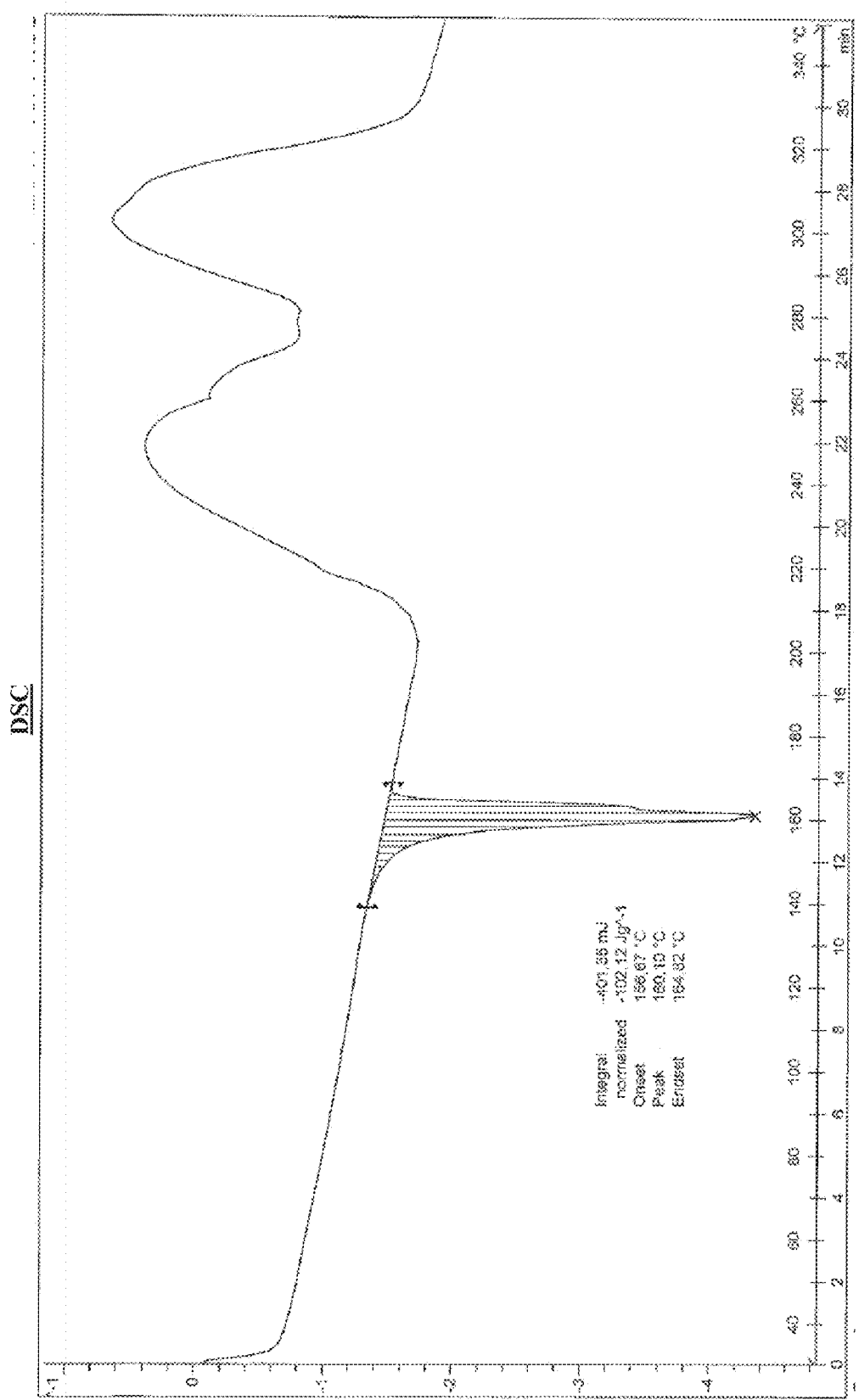
FIG. 8 shows the DSC curve of compound (IIIb).

In nitrogen atmosphere, maintaining a temperature of 0°-5° C., a solution of the mixture (III, X═Cl) in toluene (160 ml, 240.7 mmol), previously prepared according to Example 3, was added to a solution of 4-nitrophenol (36.8 g, 264.8 mmol) in acetonitrile (180 ml) and triethylamine (53.6 g, 529.5 mmol) and cooled to 0°-5° C. At complete addition, the yellow suspension was maintained under stirring for at least 1 h at 5°-10° C. A sample of the compound (IIIb) was isolated after salt filtration, concentration to small volume and trituration in isopropyl acetate. The product was characterized by IR (FIG. 7), DSC (FIG. 8) and NMR as below reported.

$^1$H-NMR (DMSO d6, 300 MHz) (δ in ppm with respect to TMS): 2.69 (3H, s, —CH$_3$); 7.50 (H-A) e 8.36 (H—B) (4H, AA'XX' system, J═9 Hz).

$^{13}$C-NMR (DMSO d$_6$, 300 MHz) (δ in ppm with respect to TMS): 11.2 (CH$_3$); 122.1 (CH-A); 125.4 (CH—B); 146.0; 151.6; 153.8; 156.0; 167.0.

Meanwhile, the suspension of the ester of compound (IIIb) above obtained was dripped to methanesulfonate of the compound of formula (II) (87 g, 202.9 mmol) previously suspended in a mixture of acetonitrile (435 ml) and triethylamine (22.6 g, 223 mmol) in nitrogen atmosphere at 65° C. During the addition (about 30 min) and during the whole reaction, the temperature was maintained at a temperature of 60°-70° C. At completion of the reaction, the suspension was distilled up to 600 ml. Ethyl acetate (500 ml), water (200 ml) and 32% HCl (14 g) were in sequence added to the dense suspension, to reach pH of about 4-4.5. The upper organic phase obtained by decanting was washed twice with water (2×110 ml). The resulting organic phase was then subjected to vacuum distillation up to 200 ml. Ethanol (250 ml) was added to the suspension and distilled again to a volume of 200 ml. The above reported treatment was repeated, then ethanol was added (250 ml) and distilled to 200 ml. The suspension was diluted with ethanol (500 ml), the temperature was raised to 60°-70° C. for at least 1 h, cooled to 0°-5° C. and maintained at this temperature for at least 1 h. The solid was isolated by filtration, washed with ethanol and dried under vacuum at 60° C. to obtain 75.4 g of Raltegravir (169.6 mmol, 83.6% yield) and HPLC purity of 99.6%.

Example 8—Preparation of Raltegravir from the Compound of Formula (III) (Wherein X═OAr Operating as in Example 7, but using an equivalent molar quantity of phenols substituted by one or more groups, equal to or different from each other and selected from halogen, cyano or nitro, instead of 4-nitrophenol, the corresponding esters of the compound (III, X═OAr) were prepared by reaction with methanesulphonate of formula (II), according to the method described in Example 7.

After reacting for 4 hours the products reported in Table 2 were obtained.

TABLE 2

| X = O—Ar | pKa | (III, X=) | (II) conversion % |
|---|---|---|---|
| 2-chloro-4-nitrophenol | 5.43 | 2-chloro-4-nitrophenoxy | 80-85 |
| 2,3,4,5,6-pentafluorophenol | 5.50 | 2,3,4,5,6-pentafluorophenoxy | 85-90 |
| 4-nitrophenol | 7.14 | 4-nitrophenoxy | ≥95 |
| 4-cyanophenol | 7.79 | 4-cyanophenoxy | ≥95 |
| 3-nitrophenol | 8.34 | 3-nitrophenoxy | ≥95 |
| 3-chlorophenol | 9.00 | 3-chlorophenoxy | 80-85 |
| 4-bromophenol | 9.34 | 4-bromophenoxy | 80-85 |

Example 9—Preparation of Raltegravir Potassium Salt

A 48% solution of KOH (1.76 ml, 22.05 mmol) was dripped in about 10 min, to a suspension of Raltegravir (10 g, 22.5 mmol) in a 1:1 mixture of ethanol/water (30 ml), cooled to 15°-20° C. The solution was filtered and ethanol (160 ml) was added in about 60 min. to the clear filtrate at the temperature of 15°-20° C. The suspension was maintained under stirring for 1 h cooled to 5° C. After 1 h the obtained product was filtered, washed with cold ethanol and dried under vacuum at 60° C., obtaining 9.9 g of Raltegravir potassium salt (20.5 mmol, 91.1% yield).

The invention claimed is:
1. A process for the preparation of raltegravir of formula (I), or a pharmaceutically acceptable salt thereof,

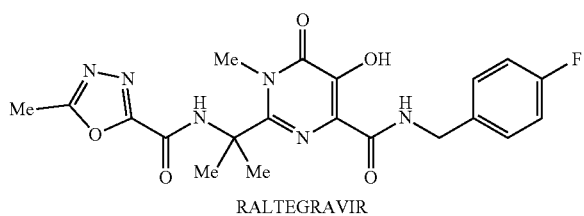

RALTEGRAVIR comprising the reaction of an unprotected compound of formula (II) in anhydrous form, or an anhydrous salt thereof,

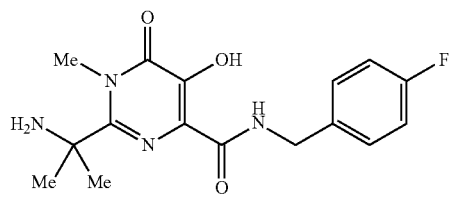

with a compound of formula (III),

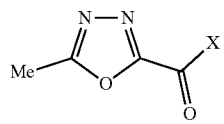

wherein
X=Cl; or
X=OAr wherein Ar is a phenyl group substituted with one or more groups, the same or different from each other, selected from halogen (F, Cl, Br or I), a cyano group or a nitro group; or
X is a substituent of formula (IV):

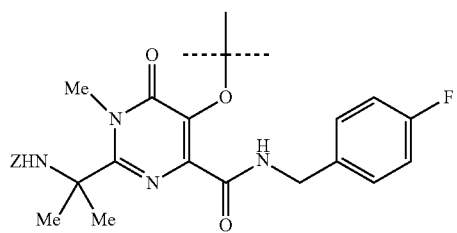

wherein Z=H (X=IVa) or Z=

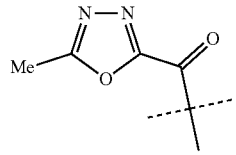

(X=IVb)
wherein the compound of formula (III) is used in amounts from 1.1 to 1.3 molar equivalent compared with the compound of formula (II);

in a reaction solvent and in the presence of one or more bases, wherein at least one base has a pKa value ≤7,4, in a total amount ranging from 1.5 to 2.9 molar equivalent compared with the compound of formula (II) or in total amount ranging from 2.5 to 3.9 molar equivalent compared with the anhydrous salt of the compound of formula (II) which is produced in situ; and
at a reaction temperature ranging from 45 to 75° C.

2. The process according to claim 1, wherein the salt of raltegravir of formula (I) is the potassium salt.

3. The process according to claim 2, wherein the salt of the compound of formula (II) is the methanesulfonate or p-toluenesulfonate salt.

4. The process according to claim 1, wherein the salt of the compound of formula (II) is the methanesulfonate or p-toluenesulfonate salt.

5. The process according to claim 1, wherein in the compound of formula (III) X=OAr is selected from the group consisting of 2-chloro-4-nitrophenol, 2,3,4,5,6-pentafluorophenol, 4-nitrophenol, 4-cyanophenol, 3-nitrophenol, 3-chlorophenol, and 4-bromophenol.

6. The process according to claim 1, wherein X=Cl or 4-nitrophenol.

7. The process according to claim 1, wherein at least one base has a pKa value ranging from 7.4 to 12.

8. The process according to claim 1, wherein the at least one base has a pKa value ranging from 8.5 to 11.5.

9. The process according to claim 1, wherein the at least one base having a pKa value ≥7.4 has formula (VI):

wherein
$R_1$, $R_2$ and $R_3$, the same or different from each other, are a straight or branched $C_1$-$C_8$ alkyl group, optionally substituted with alkoxy, dialkylamino or phenyl groups; or one of $R_1$, $R_2$ and $R_3$ is an aromatic heterocyclic ring; or $R_1$ and $R_2$ taken together with the nitrogen atom form a non-aromatic heterocyclic ring.

10. The process according to claim 9, wherein the base is selected from the group consisting of tetramethylethylenediamine, triethylamine, diisopropylethylamine, and 4-dimethylaminopyridine.

11. The process according to claim 1, wherein the solvent is selected from acetonitrile or toluene or mixtures thereof.

12. The process according to claim 1, wherein the reaction temperature ranges from 55° C. to 65° C.

13. The process according to claim 1, wherein the reaction temperature ranges from 50° C. to 60° C.

14. The process according to claim 1 for the preparation of raltegravir having formula (I), or a pharmaceutically acceptable salt thereof,

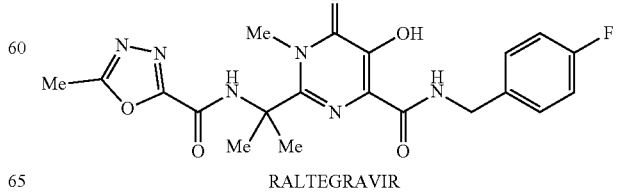

RALTEGRAVIR comprising the reaction of a compound of formula (IIa) or (IIb)

(IIa)

(IIb)

with a compound of formula (III), (III)

wherein X is as defined in claim 1.

15. The process according to claim 14, wherein the compound of formula (III) is the compound of formula (IIIa):

(IIIa)

16. The process according to claim 14, wherein the compound of formula (III) is the compound of formula (IIIb):

(IIIb)

17. A process for the preparation of raltegravir having the following formula (I), or a salt thereof, (I)

RALTEGRAVIR comprising providing a compound of formula (IIa) or (IIb), and/or (IIIb), (IIa)

(IIb)

(IIIb)

and utilizing the compound of formula (IIa) or (IIb), and/or (IIIb) to prepare the raltegravir.

18. 2-(2-Aminoprop-2-yl)-N-(4-fluorobenzyl)-5-hydroxy-1-methyl-6-oxo-1,6-dihydropyrimidine-4-carboxamide methanesulfonate of formula (IIa)

(IIa)

19. 2-(2-Aminoprop-2-yl)-N-(4-fluorobenzyl)-5-hydroxy-1-methyl-6-oxo-1,6-dihydropyrimidine-4-carboxamide para-toluenesulfonate of formula (IIb)

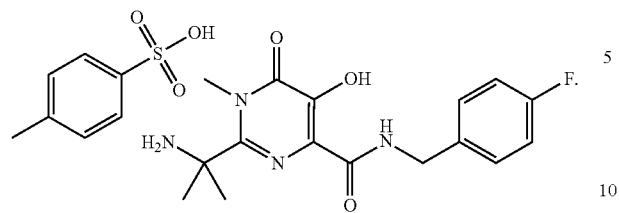
20. 4-Nitrophenoxy ester of 2-[5-methyl-1,3,4-oxadiazolyl] carboxylic acid of formula (IIIb)
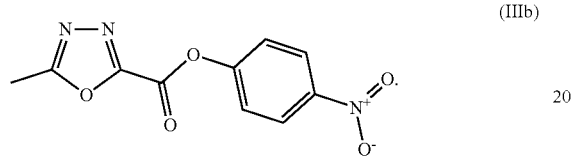
* * * * *